US008025831B2

(12) United States Patent
Kong et al.

(10) Patent No.: US 8,025,831 B2
(45) Date of Patent: Sep. 27, 2011

(54) IMPRINTING OF SUPPORTED AND FREE-STANDING 3-D MICRO- OR NANO-STRUCTURES

(75) Inventors: Yen Peng Kong, Singapore (SG); Hong Yee Low, Singapore (SG); Stella W. Pang, Ann Arbor, MI (US); Albert F. Yee, Irvine, CA (US)

(73) Assignees: Agency for Science, Technology and Research, Singapore (SG); The Regents of University of Michigan, Ann Arbor, MI (US)

( * ) Notice: Subject to any disclaimer, the term of this patent is extended or adjusted under 35 U.S.C. 154(b) by 2426 days.

(21) Appl. No.: 10/852,448

(22) Filed: May 24, 2004

(65) Prior Publication Data
US 2005/0258570 A1    Nov. 24, 2005

(51) Int. Cl.
- *B27N 3/08* (2006.01)
- *B28B 5/00* (2006.01)
- *A61M 25/00* (2006.01)
- *B28B 5/02* (2006.01)
- *B32B 3/00* (2006.01)
- *B32B 5/16* (2006.01)

(52) U.S. Cl. ............... 264/297.4; 264/239; 264/241; 264/250; 264/264; 264/293; 264/294; 264/308; 428/156; 428/327

(58) Field of Classification Search ............... 264/239, 264/241, 250, 264, 293, 294, 297.4, 308; 428/156, 327
See application file for complete search history.

(56) References Cited

U.S. PATENT DOCUMENTS
- 5,512,131 A * 4/1996 Kumar et al. ............ 438/738
- 6,375,870 B1 * 4/2002 Visovsky et al. ......... 264/1.31
- 6,860,956 B2 * 3/2005 Bao et al. ................. 156/232

(Continued)

FOREIGN PATENT DOCUMENTS
- WO    WO 03/096123 A1 *  8/2002
- WO    WO 03/079416 A1     9/2003
- WO    WO 03/096123 A1     11/2003

OTHER PUBLICATIONS

Bao et al. ("Nanoimprinting over topography and multilayer three-dimensional printing," J. Vac. Sci. Technol. B, 20:2881-2886 (2002).*

(Continued)

*Primary Examiner* — Monica Huson
*Assistant Examiner* — Michael Piery
(74) *Attorney, Agent, or Firm* — Winstead PC

(57) ABSTRACT

The present invention is directed to micro- and nano-scale imprinting methods and the use of such methods to fabricate supported and/or free-standing 3-D micro- and/or nano-structures of polymeric, ceramic, and/or metallic materials. In some embodiments, a duo-mold approach is employed in the fabrication of these structures. In such methods, surface treatments are employed to impart differential surface energies to different molds and/or different parts of the mold(s). Such surface treatments permit the formation of three-dimensional (3-D) structures through imprinting and the transfer of such structures to a substrate. In some or other embodiments, such surface treatments and variation in glass transition temperature of the polymers used can facilitate separation of the 3-D structures from the molds to form free-standing micro- and/or nano-structures individually and/or in a film. In some or other embodiments, a "latch-on" assembly technique is utilized to form supported and/or free-standing stacked micro- and/or nano-structures that enable the assembly of polymers without a glass transition temperature and eliminate the heating required to assemble thermoplastic polymers.

3 Claims, 8 Drawing Sheets

U.S. PATENT DOCUMENTS

| | | | |
|---|---|---|---|
| 7,037,639 B2 * | 5/2006 | Voisin | 430/316 |
| 2004/0219249 A1 | 11/2004 | Chung et al. | |
| 2004/0231781 A1 | 11/2004 | Bao et al. | |
| 2005/0116370 A1 | 6/2005 | Ogino et al. | |

OTHER PUBLICATIONS

Office Action for U.S. Appl. No. 11/436,833 dated Jul. 31, 2009, pp. 1-11.

* cited by examiner

US 8,025,831 B2

IMPRINTING OF SUPPORTED AND FREE-STANDING 3-D MICRO- OR NANO-STRUCTURES

TECHNICAL FIELD

The present invention relates in general to micro- and nano-imprinting techniques, and in particular, to the use of novel micro- and nano-imprinting techniques for the purpose of making supported and free-standing three-dimensional micro- and nano-structures.

BACKGROUND INFORMATION

Conventional photolithography is believed to be limited to about 150 nm in pattern dimensions. While X-ray and ion beam lithography have been demonstrated as viable alternative techniques for creating pattern dimensions below this limit, they are expensive. E-beam lithography has also been proven as a viable technique. However, it is time consuming and, like X-ray and ion beam lithography, expensive. In contrast to such lithographic techniques, imprinting offers an attractive alternative to the fabrication of two-dimensional (2-D) nanometer-scale features, as a result of simpler, faster, and cheaper processing, making this technique a potential replacement for photolithography in mass production.

The above-mentioned lithographic techniques are further limited to fabrication of 2-D and supported features. Imprinting, however, can lend itself to the fabrication of three-dimensional (3-D) features, wherein 3-D features comprise structural variation with depth. Three-dimensional patterning techniques are likely to be important enabling technologies for a number of applications. In microelectronics, for example, the third dimension could possibly allow the speed and memory of microprocessors to go beyond the limitations currently imposed by 2-D features. In optoelectronic industries, 3-D photonic band gap structures are garnering considerable attention because 3-D structures serve to minimize loss of light [Kiriakidis et al., "Fabrication of 2-D and 3-D Photonic Band-Gap Crystal in the GHz and THz Region," *Mater. Phys. Mech.*, 1:20-26, 2000]. In drug/chemical delivery systems, sensing systems and catalysis, the feasibility of fabricating 3-D structures will provide breakthroughs in the efficiency of controlled delivery, sensing, and selectivity in chemical reactions. For example, a sphere with a meshed surface can be envisioned as a chambered pill that contains multiple drugs or a multifunctional catalysis support.

While 2-D fabrication techniques are mature technology down to the sub-micrometer scale, very little has been reported regarding 3-D sub-micrometer fabrication techniques. Currently, of the limited amount of literature available on sub-micrometer 3-D fabrication techniques, most reports are seen to be mere extensions of various photolithography techniques. For instance, Whitesides et al. have shown that a porous microsphere can be obtained via a self-assembly approach [Huck et al., "Three-Dimensional Mesoscale Self-Assembly," *J. Am. Chem. Soc.*, 129:8267-8268, 1998], and Yamamoto et al. have demonstrated the fabrication of micrometer scale grooved structures using deep X-ray lithography [Tabata et al., "3D Fabrication by Moving Mask Deep X-ray Lithography with Multiple Stages," The Fifteenth IEEE International Conference on Micro Electro Mechanical Systems, 180-183, 2002]. Whitesides et al. have also reported on a "membrane folding" method used to create 3-D structures [Brittain et al., "Microorigami: Fabrication of Small Three-Dimensional Metallic Structures," *J. Phys. Chem. B*, 105:347-350, 2001]. While most of these techniques have demonstrated the feasibility of creating 3-D sub-micrometer or nanometer scale features, they are not easily implemented for mass production.

Both conventional nano-imprinting [Sun et al., "Multilayer resist methods for nanoimprint lithography on nonflat surfaces," *J. Vac. Sci. Technol. B,]*6(6):3922-3925, 1998] and reversal imprinting [Huang et al., "Reversal imprinting by transferring polymer from mold to substrate," *J. Vac. Sci. Technol. B*, 20(6):2872-2876, 2002] techniques are attractive alternatives to the above-mentioned techniques in the fabrication of 3-D nano-features, although currently both techniques create 3-D structures through multiple imprinting on patterned substrates or on substrates with topology. A more efficient imprinting technique would, therefore, go a long way in solidifying imprinting's role as a potential replacement for currently used lithographic patterning techniques.

SUMMARY OF THE INVENTION

The present invention is directed to micro- and nano-scale imprinting methods and the use of such methods to fabricate supported and/or free-standing 3-D micro- and/or nano-structures of polymeric, ceramic, and/or metallic materials.

In some embodiments of the present invention, a duo-mold approach is employed in the above-described methods. In some embodiments, surface treatments are employed to impart differential surface energies to different molds and/or different parts of the mold(s). Such surface treatments, often in combination with differences in polymer glass transition temperatures, permit the formation of three-dimensional (3-D) micro- and/or nano-structures through imprinting and the transfer of such structures to a substrate. In some or other embodiments, such surface treatments can facilitate separation of the 3-D structures from the molds to form free-standing micro- and/or nano-structures individually and/or in a film. In some embodiments, such surface treatments can involve silanes, coatings, plasma deposition or treatment, and/or grafting treatments.

In some embodiments of the present invention, supported or free-standing stacked 3-D micro- and/or nano-structures are fabricated by using polymers of progressively lower glass transition temperatures or with miscible polymer blends. In some or other embodiments, a "latch-on" assembly technique is utilized to form supported and/or free-standing stacked micro- and/or nano-structures that enable the assembly of polymers without a glass transition temperature and eliminate the heating required to assemble thermoplastic polymers.

The present invention provides for novel methods in which to imprint supported and/or free-standing 3-D micro- and/or nano-structures. Such novel methods have a number of advantages over the existing prior art. First, the present invention provides for a direct patterning methods that do not require a sacrificial layer/component—as in most methods found in the existing art. This allows for fewer processing steps. Second, the present invention provides for direct patterning methods that allow the formation of cavities with completely sealed edges. Third, the present invention allows for the patterning of well-defined 3-D structures with nano-scale dimensions, wherein such 3-D structures can be transferred to a substrate, or lifted-off as a free standing film or as individual 3-D structures. Fourth, the present invention provides for a variety of 3-D micro- and/or nano-structures that can be imprinted, stacked, and/or assembled.

In addition to the advantages described above, the present invention also overcomes the limitations of the prior art in a number of ways. First, the duo-mold approach of the present invention eliminates the need for a sacrificial layer/component used by numerous prior art approaches to form 3-D structures. Second, the duo-mold approach enables the formation of closed structures that cannot be fabricated using conventional sacrificial layer/component techniques. Third, surface treatment of the molds that result in a differential surface energy permits selective imprinting and demolding and also allows for the eventual transfer of the structure onto a substrate. Fourth, fewer processing steps are required compared to conventional photolithography based techniques for 3-D structure fabrication. Fifth, the present invention provides for a variety of possible 3-D structures, such that the techniques is potentially applicable for fabrication of 3-D microelectronics, micro-electromechanical systems/nano-electromechanical [systems] (MEMS/NEMS) devices and photonic bandgap structures.

The present invention finds potential application in the areas of MEMS and NEMS devices (fluidics, actuators, lenses, resonators), sensors, integrated chip devices, photonic band gap structures (waveguides), and in drug/chemical delivery systems. This diversity of potential applications attests to the significance of the methods and processes of the present invention.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
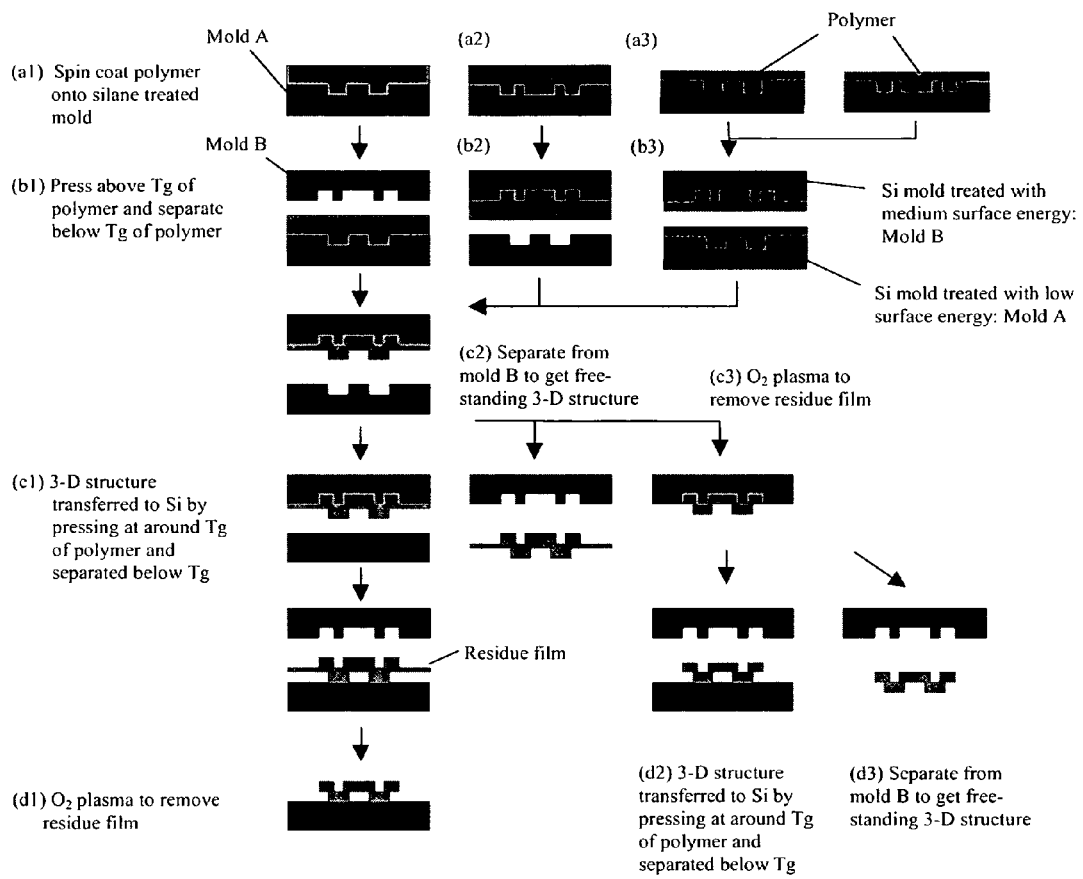
FIG. 1 schematically illustrates the duo-mold imprinting processes of embodiments of the present invention in a generalized manner.

The present invention is directed to micro- and nano-scale imprinting methods and the use of such methods to fabricate supported and/or free-standing 3-D micro- and/or nano-structures of polymeric, ceramic, and/or metallic materials. While the making and/or using of various embodiments of the present invention are discussed below, it should be appreciated that the present invention provides many applicable inventive concepts that may be embodied in a variety of specific contexts. The specific embodiments discussed herein are merely illustrative of specific ways to make and/or use the invention and are not intended to delimit the scope of the invention.

While most of the terms used herein will be recognizable to those of skill in the art, the following definitions are nevertheless put forth to aid in the understanding of the present invention. It should be understood, however, that when not explicitly defined, terms should be interpreted as adopting a meaning presently accepted by those of skill in the art.

"Micro-structures," according to the present invention, are structures comprising "micro-scale" features; micro-scale features being defined herein as features having dimensions that range in length from about 1 micrometer (μm) to about 100 μm.

"Nano-structures," according to the present invention, are structures comprising "nano-scale" or "sub-micron" features; nano-scale features being defined herein as features having dimensions below about 1 μm.

"Three-dimensional," abbreviated "3-D" and as defined herein, refers to structures or structural features that vary (structurally) with depth.

"Surface energy," as defined herein, is a surface characteristic associated with the molecular forces of a particular surface, generally in contact with some other material and generally measured in $mJ/m^2$. "Differential surface energy," according to the present invention, merely refers to dissimilar surface energies between two or more materials. For the methods described herein, "low surface energy" generally means<12 $mJ/m^2$, "medium surface energy" generally means about 14-30 $mJ/m^2$, and "high surface energy" generally means>50 $mJ/m^2$.

A "duo-mold" process, as defined herein, refers to processes of the present invention wherein two molds, generally with different surface coatings to impart different surface energies, are used to fabricate polymeric 3-D micro- and/or nano-structured objects.

"Spin-coating," as defined herein, generally refers to a process wherein a polymer solution is dispersed on a surface (e.g., a mold) and the surface is rapidly spun centrifugally forcing the solution to spread out and forming a thin layer of de-solvated polymer in the process.

"Glass-transition temperature," abbreviated $T_g$ and as defined herein, is the temperature at which many high polymers change from a hard vitreous state to a plastic state. Above this temperature, such polymers can be said to flow. Note, however, that not all polymers and polymer blends have a $T_g$.

"Plasma cleaning," according to the present invention, generally refers to exposure of a surface to a plasma such that only the top most layers are removed. Generally such plasma is a low-pressure oxidative plasma such as oxygen ($O_2$) generated with a RF or microwave source. "Plasma etching," according to the present invention, generally comprises the same principles as plasma cleaning, but is more aggressive—leading to a greater amount of removal.

"Latch-on" assembly mechanisms, as defined herein, generally refer to mechanical attachment mechanisms similar to the attachment mechanisms employed by Lego® blocks, for the purposes of assembling superstructures comprised of 3-D micro- and/or nano-structures.

In some embodiments of the present invention, a duo-mold approach is employed in the above-described methods. In some embodiments, surface treatments are employed to impart differential surface energies to different parts of the mold(s). Such surface treatments permit the formation of three-dimensional (3-D) structures through imprinting and the transfer of such structures to a substrate. In some or other embodiments, such surface treatments can facilitate separation of the 3-D structures from the molds to form free-standing 3-D micro- and/or nano-structures individually and/or in a film.

The present invention provides for the imprinting of supported and free-standing three-dimensional (3-D) objects with micro- and/or nano-scale features. Using a duo-mold imprinting process, well-defined supported and free-standing 3-D micrometer (μm) and nanometer (nm) features can be fabricated. A generalized illustration of the duo-mold imprinting process (Process I) is shown in FIG. 1. Referring to FIG. 1, step a1, a patterned silicon (Si) mold (mold A) is treated with a low surface energy silane, for example perfluorodecyltrichlorosilane (FDTS), octadecyltrichlorosilane (OTS) or octadecylmethyldichlorosilane (ODS). Typically, the surface treatment is performed in a nitrogen/inert gas glove box or in an environment where the relative humidity of the atmosphere is low (<20% RH). The silanes are dissolved in an anhydrous organic solvent such as n-heptane to a concentration of 20 mM. The silicon mold, oxygen plasma cleaned, is immersed in the silane solution for 10 minutes. On completion of the treatment, the mold is rinsed with n-heptane and blow dried with dry nitrogen gas. A polymer solution, for example a poly(methyl methacrylate) (PMMA) in toluene, is then spin-coated onto the silane-treated mold A such that it fills up the trenches and forms a planarized thin film (FIG. 1, step a1). The choice of surface treatment and the polymers are interrelated, and judicious selection is needed in order to obtain a planarized film. For example, when the combination of FDTS (for surface treatment) and PMMA (spin-coated polymer) are used, PMMA dissolved in toluene or propylene glycol methyl ether acetate (PGMEA) will give a uniform coating. The molds described herein may be fabricated by a variety of techniques including, but not limited to, photolithography, holographic lithography, e-beam lithography, ion-beam lithography, and combinations thereof.

A second Si mold (mold B) is treated with a silane, for example phenethyltrichlorosilane (PETS), phenethylmethyltrichlorosilane (PEDS) or a sequential treatment of PEDS or ODS and then FDTS in order to obtain a medium surface energy. Typically, the surface treatment is performed in a nitrogen/inert gas glove box or in an environment where the relative humidity of the atmosphere is low (<20% RH). The silanes are dissolved in an anhydrous organic solvent such as n-heptane to a concentration of 20 mM. The silicon mold, oxygen plasma cleaned, is immersed in the silane solution for 10 minutes. On completion of the treatment, the mold is rinsed with n-heptane and blow dried with dry nitrogen gas. A second treatment with another 20 mM silane solution for 10 minutes is carried out for molds that require a sequential silane treatment. On completion of the second treatment, the mold is rinsed with n-heptane and blow dried with dry nitrogen gas. Mold B is then aligned and pressed at a suitable pressure onto the polymer-coated mold A at a temperature above the glass transition temperature ($T_g$) of the polymer. Mold B is then separated below the $T_g$ of the polymer, thus forming a 3-D structure and resulting in the transfer of the polymer film from mold A to mold B (FIG. 1, step b1). This transfer is made possible by the difference in surface energies of the two molds. Since mold B has a surface energy higher than the surface energy of mold A, the polymer film preferentially adheres to mold B and thus results in the transfer of the polymer film.

Additionally or alternatively, in some embodiments the process can be carried out by spin coating the polymer onto mold B instead of mold A (Process II). In such embodiments, there is no transfer of the polymer film from mold A to mold B, since mold B has a higher surface energy. Thus, mold A will imprint onto the polymer film on mold B (FIG. 1, steps a2 and b2).

Additionally or alternatively, in some embodiments the process can be carried out by spin coating the polymer onto both molds A and B (Process III). The coatings can be of similar or of dissimilar materials. In such embodiments, the polymer film from mold A adheres to the polymer film on mold B when the molds are pressed together at a temperature above the $T_g$ of either polymer. Since mold B has a higher surface energy, the polymer film preferentially adheres to mold B and thus results in the transfer of the polymer film from mold A to mold B (FIG. 1, steps a3 and b3).

With the polymer film on mold B, it is possible to carry out three generalized sub-processes, as described below.

Sub-Process A: Mold B may be pressed at a suitable pressure onto an $O_2$ plasma-cleaned blank Si substrate at a temperature that is close to the $T_g$ of the polymer. Mold B is then separated at a temperature below the $T_g$ of the polymer which results in the transfer of the polymer film (now a 3-D structured polymer film) to the Si substrate (FIG. 1, step c1). An $O_2$ plasma etch may then be employed to remove the residue layer of the polymer film (FIG. 1, step d1). This results in a final 3-D polymeric structure with micro- and/or nano-scale dimensions.

Sub-Process B: Alternatively, a free-standing 3-D polymeric structure can be formed by separating the polymer film from mold B (FIG. 1, step c2). The polymer film may then be separated from mold B by etching the silicon oxide, metal, or metal oxide (of which the mold is comprised) in a solution (e.g., hydrofluoric acid).

Sub-Process C: A third alternative is to use an $O_2$ plasma etch to remove the residue layer while the polymer film is still attached to mold B. The 3-D polymeric structure can then be transferred to a Si substrate as in Sub-process A (FIG. 1, step d2) or separated from mold B as in Sub-Process B (FIG. 1, step d3).

A key factor in the success of these processes lies in the selection of the silane treatments that enable the transfer of the polymer film from one Si mold to another, and which serve to facilitate the final release from the mold to form either supported or free-standing 3-D structures. Such selectively-applied silane treatments provide for the differential surface energies that make these processes viable.

Surface energy manipulation is a simple and convenient way of determining which surface the patterned polymer film will adhere to. In using such surface energy manipulation, it is generally assumed that the surface areas in contact with the patterned polymer film are similar. To more accurately determine which surface the patterned polymer film will adhere to, the work of adhesion per unit area (or work of separation per unit area) between the polymer and the surface should be calculated. The amount of work needed to separate is obtained by multiplying the surface area of the mold by the work of adhesion per unit area. The patterned polymer film will remain on the mold with the larger work required to separate.

Structural Assemblies

In some embodiments of the present invention, 3-D micro- and/or nano-structures, made by the above-described methods, are assembled into larger "super structures." Such assemblies can be fabricated by taking advantage of differential surface energies and glass transition temperatures to transfer polymeric 3-D micro- and/or nano-structures to previously-deposited polymeric 3-D micro- and/or nano-structures to form layers or assemblies of such 3-D micro- and/or nano-structures. Alternatively, such assemblies can be fabricated using a "latch-on" mechanism that eliminates the need for using polymers with glass transition temperatures.

Figure 4:
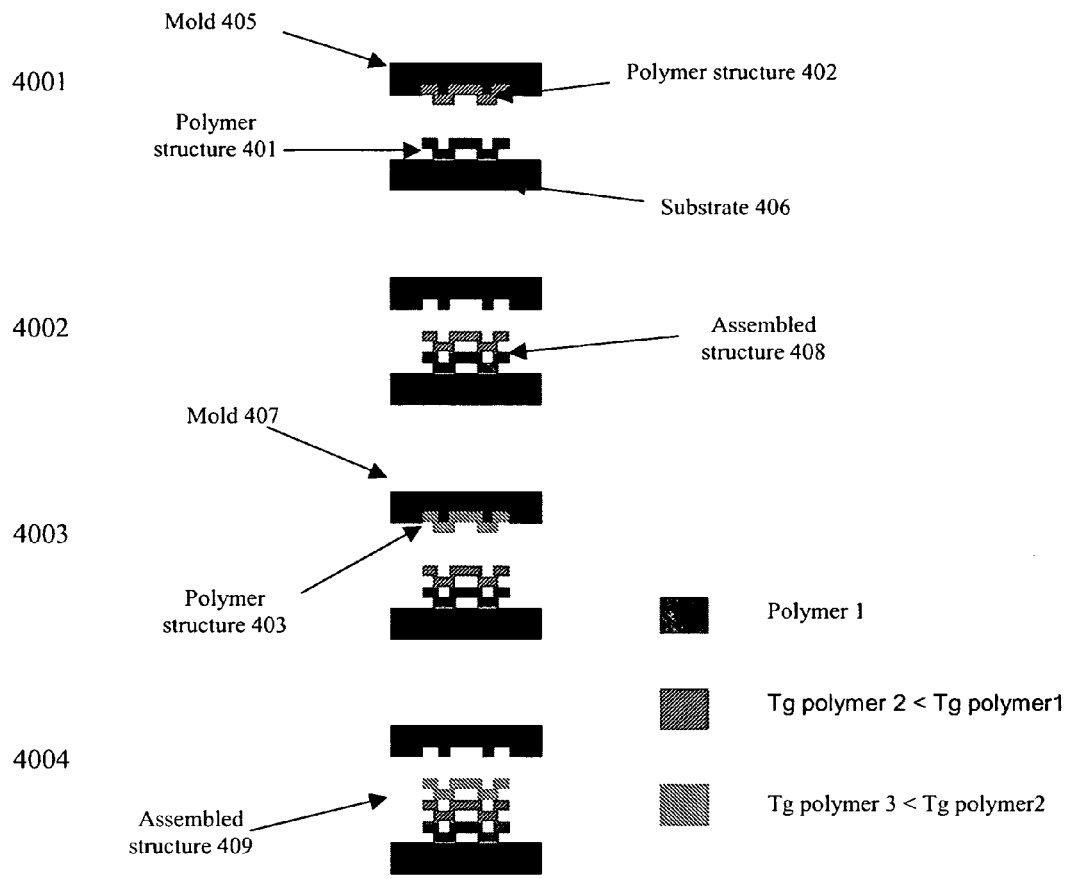
FIG. 4 depicts stacked 3-D polymeric micro- or nano-structures formed by using polymers with progressively lower $T_g$.

In some embodiments, supported or free-standing stacked 3-D micro- and/or nano-structures are fabricated by using polymers of progressively lower glass transition temperatures ($T_g$s), or by using miscible polymer blends. Referring to FIG. 4, to a previously-deposited polymeric structure 401 comprising a $T_o$ and residing on substrate 406, silane-treated mold 405, containing a polymeric structure 402 comprising a $T_{g2}$ (where $T_{g2}<T_{g1}$), is pressed onto polymeric structure 401 at a temperature that is above $T_{g2}$, but below $T_{g1}$ (step 4001). In step 4002, mold 405 is separated from polymeric structure 402 at a temperature that is above $T_{g2}$, leading to the formation of assembled structure 408. Additional structures can be added, as shown in step 4003, wherein silane-treated mold 407, containing a polymeric structure 403 comprising a $T_{g3}$ (where $T_{g3}<T_{g2}$), is pressed onto polymeric structure 402 (as part of assembled structure 408) at a temperature that is above $T_{g3}$, but below $T_{g2}$. Mold 407 is then separated from polymeric structure 403 at a temperature that is below $T_{g3}$ to form augmented assembled structure 409 (step 4004). Such assembling can be continued provided that each successive polymeric structure added has a progressively lower $T_g$.

The physical properties of polymer blends can be tuned such that when the temperature is raised close to the $T_g$ of the polymer blend, plastic deformation of the polymer blend structures are reduced or minimized under pressure. Thus several layers of the same polymer blend can be transferred on top of one another without the previous layers undergoing deformation. Thus, in some embodiments, using polymer blends eliminates the need to use polymers with progressively lower $T_g$s to form stacked 3-D structures. The use of polymer blends is clearly an advantageous and enabling approach when forming stacked structures having a multiplicity of stacked layers. Another advantage of using polymer blends is the ability of reducing the imprinting and transfer temperature by lowering the onset of the glassy state transition. For example, by using a symmetric blend of PMMA and poly (vinyl acetate) it is possible to imprint and transfer the patterns at 45° C.

Figure 5:
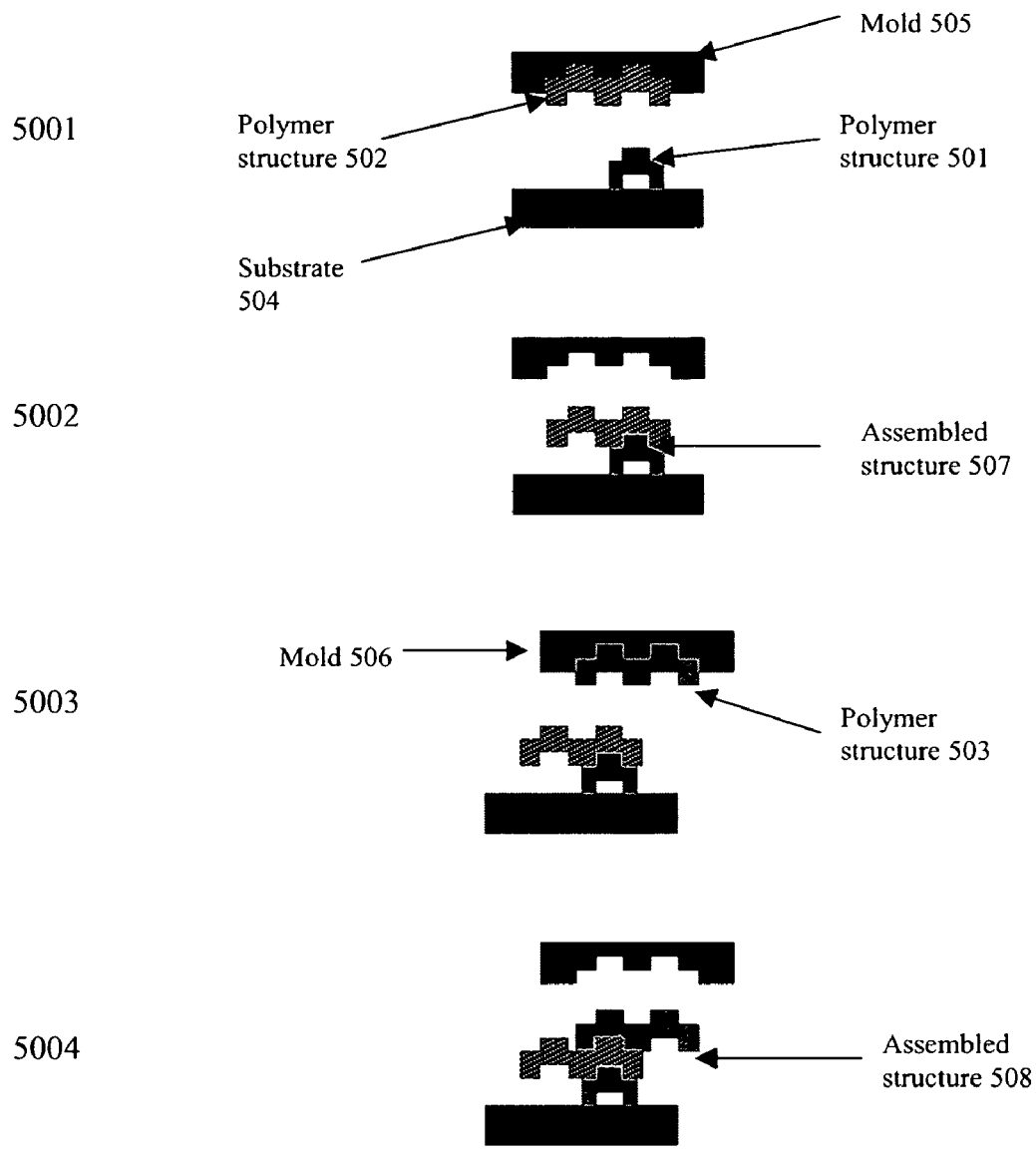
FIG. 5 depicts an assembly of 3-D polymeric micro- or nano-structures using a latch-on mechanism similar to Lego® bricks.

In some or other embodiments, a "latch-on" assembly technique is utilized to form supported and/or free-standing stacked micro- and/or nano-structures that enable the assembly of polymers that lack a glass transition temperature and eliminate the heating required to assemble thermoplastic polymers. Referring to FIG. 5, step 5001, to a polymeric structure 501, residing on substrate 504, polymeric structure 502, contained within mold 505, is aligned and pressed into polymeric structure 501 such that the two structures interlock via a "latch-on" process similar to that employed by Lego® toy building blocks. In step 5002, mold 505 is removed to provide assembled structure 507. In step 5003, the process is repeated with mold 506 transferring polymeric structure 503 to the assembled structure 507. Release of mold 506 (step 5004) yields augmented assembled structure 508. Such assembling can be continued repeatedly to provide large superstructures and/or structural arrays comprising 3-D micro- and/or nano-structural building blocks. The molds are silane-treated to enable the release of the structures. The polymeric structure 501 is first formed using the duo-mold process prior to transferring it to substrate 504. The polymeric structure 502 is first formed using the duo-mold process and is here illustrated as still contained within mold 505. Mold 505 is silane-treated and corresponds to mold B of FIG. 1.

Variations

Figure 6:
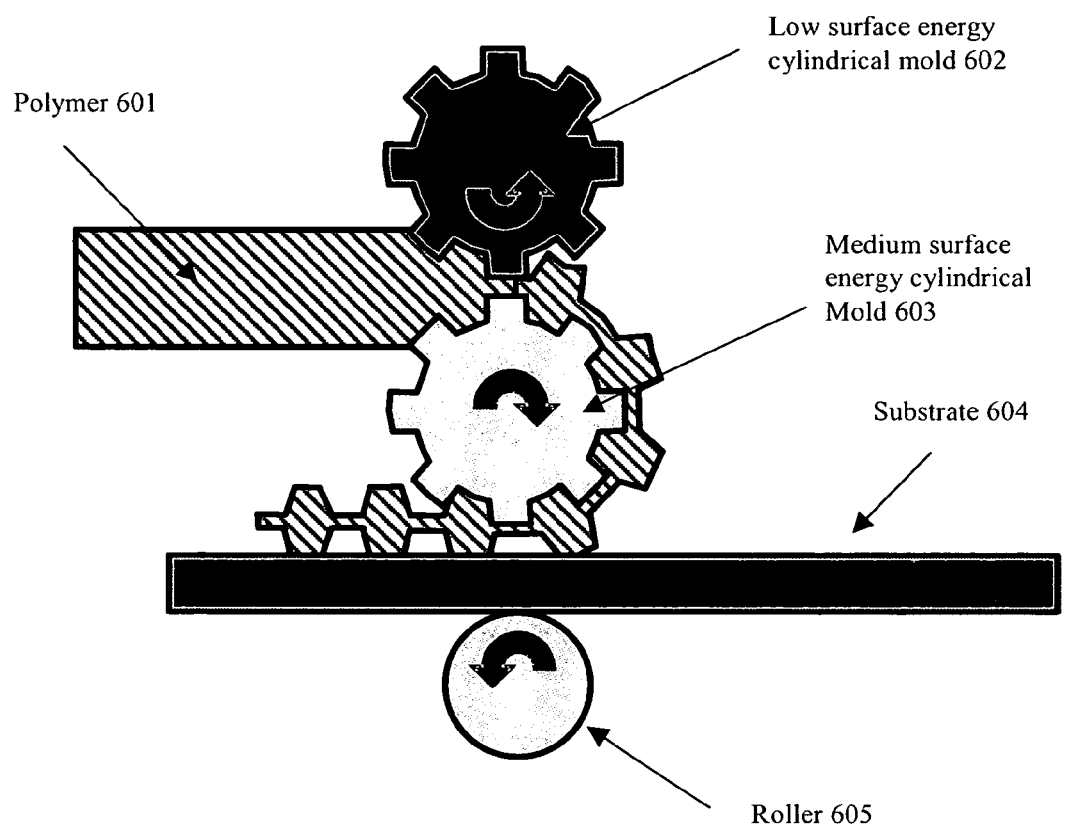
FIG. 6 depicts a reel to reel process for scaling up the duo-mold processes according to some embodiments of the present invention.

The foregoing descriptions seemingly demonstrate the methods on a small scale or on a mold-pair that produces one particular structure. However, the processes above can be scaled up using several methods:

a) Step and repeat. With the step and repeat method, mold-pairs up to 3 inches by 3 inches can be repeatedly used to imprint and transfer the 3-D polymeric structures to a larger substrate.

b) Wafer sized mold-pairs (up to 6 inches in diameter). With wafer sized mold-pairs, the patterns can be repeated to form multiple 3-D structures on a wafer sized substrate.

c) Reel to reel process. As illustrated in FIG. 6, a reel to reel process can scale up the duo mold process significantly. Cylinders can be patterned to form cylindrical molds and the cylindrical molds can be treated to obtain low surface energy molds and medium surface energy molds. Polymer sheets 601 can be fed in between the cylindrical molds 602 and 603 or one of the molds can be dip coated. The process can be carried out in a heated chamber and a constant pressure between the two cylindrical molds maintained. A sheet can then be fed between the medium surface energy mold and a roller 605 to finally transfer the patterned polymer film onto the substrate.

To form ceramic or metal-ceramic 3-D micro- and nano-structures, a sol-gel based process can be used to spin coat the ceramic or metal-ceramic precursors (hydrolyzable molecular precursors, mostly metal or semi-metal alkoxides) onto the molds. The duo mold process is then carried out with the spin coated sol-gel at a temperature that will pyrolyze the organics and ultimately form the ceramic or metal-ceramic 3-D structures.

The following examples are provided to demonstrate particular embodiments of the present invention. It should be appreciated by those of skill in the art that the methods disclosed in the examples which follows merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

This Example serves to illustrate some types of 3-D microstructures that can be formed using methods of the present invention.

Figure 2:
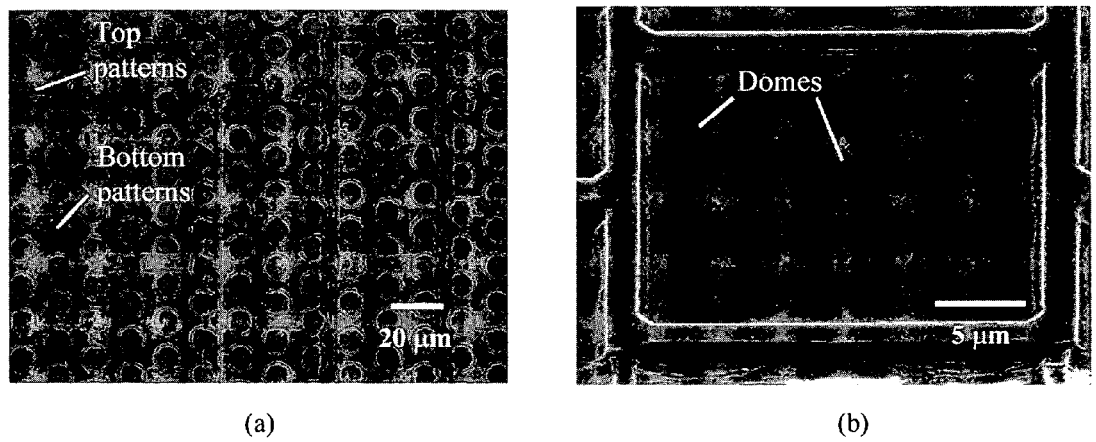
FIGS. 2A and B depict (A) an optical micrograph of a 3-D structure comprising 20 μm wide squares on top and 5 μm diameter circles below, and (B) an SEM image of the 3-D structure, wherein the scanning electron beam produces a "doming" of the micro-structures.

FIG. 2A depicts an optical micrograph of an imprinted 3-D structure supported on a Si substrate comprised of 20 μm wide squares on the top and 5 μm diameter circular cavities on the bottom, wherein such structures are produced by duo-mold imprinting methods of the present invention. The structures are fabricated according to the following steps:

1) Mold A is a Si mold comprising 5 μm diameter circular pillars of height 900 nm. Mold A is treated with a 20 mM silane solution (in n-heptane) of FDTS that results in a low surface energy mold. Note that in this Example, molds A and B have been pre-patterned with conventional photolithography, wherein the patterns are transferred onto the silicon with a plasma etch.

2) Mold B is a Si mold comprising 20 μm wide squares of height 900 nm. Mold B is treated sequentially with PEDS and ODS solutions that results in a medium surface energy mold. Typically, the surface treatment is performed in a nitrogen/inert gas glove box or in an environment where the relative humidity of the atmosphere is low (<20% RH). The silanes are dissolved in an anhydrous organic solvent such as n-heptane to a concentration of 20 mM. The silicon mold, oxygen plasma cleaned, is immersed in PEDS solution for 10 minutes. On completion of the treatment, the mold is rinsed with n-heptane and blow dried with dry nitrogen gas. A second sequential treatment with ODS solution for 10 minutes is carried out. On completion of the second treatment, the mold is rinsed with n-heptane and blow dried with dry nitrogen gas.

A 9 wt. % PMMA (average molecular weight (MW) ~350 kg/mol) in PGMEA solution is spin coated at 3000 rpm for 30 seconds on mold A to obtain a planarized coating of around 900 nm thickness (as in FIG. 1, step a1). The PMMA-coated mold A is then baked at 80° C. for 3 minutes to remove any remaining solvent in the film. Mold B is then aligned and pressed onto the PMMA-coated mold A with a pressure of 60 bars at 180° C. Ten minutes later, the molds are cooled down to 70° C. and separated (as in FIG. 1, step b1). This results in the transfer of the patterned PMMA film from mold A to mold B. Mold B, now comprising the patterned PMMA film, is then pressed onto an $O_2$ plasma-cleaned blank Si substrate at 95° C. for 3 minutes before cooling it down to 70° C. where mold B is separated from the Si substrate. The patterned PMMA film is transferred to the Si substrate thus resulting in a supported 3-D polymeric structure (FIG. 1, step c1).

The scanning electron microscopy (SEM) micrograph shown in FIG. 2B illustrates the square patterns and domes defined by the underlying circular patterns. The domes are formed during the scanning of the electron beam on the imaged area at a high magnification. While not intending to be bound by theory, the dome formation process might be due to outgassing of the solvent upon electron irradiation. A reduction in the thickness of the irradiated polymer was also noted. These doming and thickness reduction phenomenon appear to be dependent on the electron dose, wherein electron dose is defined herein as the number of electrons per unit area per unit time.

EXAMPLE 2

This Example serves to illustrate an embodiment that falls within the context of sub-process B, described above.

Figure 3:
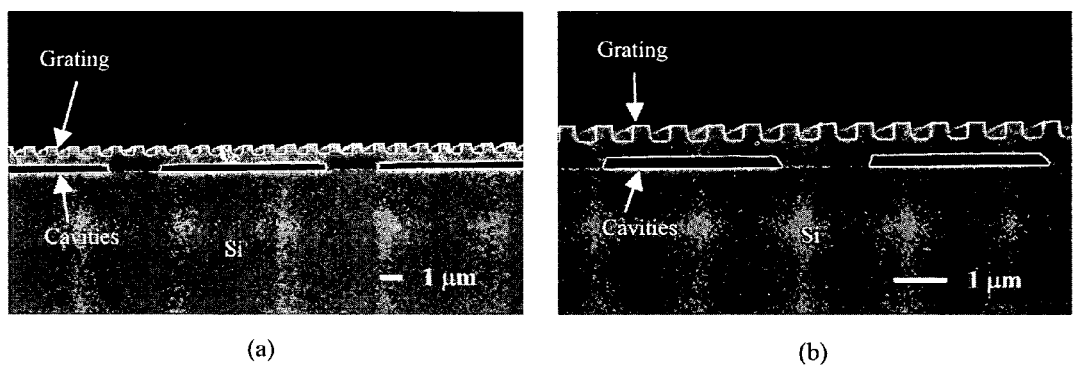
FIGS. 3A and B depict 3-D polymeric nano-structures of a 700 nm pitch grating with a 1:1 duty cycle on top of 5 μm (A) and 3 μM (B) wide square cavities.

FIG. 3 illustrates an example of an imprinted 3-D structure supported on Si. The structure comprises a grating of 700 nm pitch with a 1:1 duty cycle on the top with 3 and 5 μm wide square cavities on the bottom. The two molds that were used to form this structure comprise the following:

1) Mold A is a Si mold of 3 and 5 μm wide squares of height 250 nm. Mold A is treated with a 20 mM silane solution (in heptane) of FDTS that results in a low surface energy mold.

2) Mold B is a Si grating mold of 700 nm pitch with a 1:1 duty cycle and height 350 nm. Mold B is also treated with a 20 mM silane solution (in heptane) of FDTS that also results in a low surface energy mold.

An 8 wt. % PMMA (average MW ~15 kg/mol) in toluene solution is spin-coated at 3000 rpm for 30 seconds onto mold B to obtain a planarized coating with a thickness of around 500 nm (as in FIG. 1, step a2). The PMMA-coated mold B is then baked at 80° C. for 3 minutes to remove any remaining solvent in the film. Mold A is then aligned and pressed onto the PMMA-coated mold B with a pressure of 50 bars at 150° C. Ten minutes later, the molds are cooled down to 50° C. and separated (as in FIG. 1, step b2). This does not result in any transfer of the patterned PMMA film as encountered in the previous example. The PMMA-coated mold B is then pressed onto an $O_2$ plasma-cleaned blank Si substrate at 80° C. for 3 minutes before cooling it down to 50° C. where mold B is separated from the Si substrate. The patterned PMMA film is then transferred to the Si substrate, thus resulting in a supported 3-D polymeric structure (as in FIG. 1, step c1).

Although both molds have been treated with the same silane to obtain a low surface energy, the film remains coated on mold B because there is a larger surface area on mold B as compared to mold A. The larger surface area results in a larger work of adhesion for mold B as compared to mold A. This results in the polymer film preferentially adhering to mold B. Therefore, to obtain the designed 3-D structures described above, one has to take into account the surface area of the molds in addition to the surface energy such that the film will adhere to the mold with the larger work of adhesion.

In both of the above-described Examples 1 and 2, such structures cannot be fabricated using conventional nano-imprinting methods which employ the use of a sacrificial layer to form the cavities since the cavities are completely sealed around the edges. In contrast, the width of the cavities that can be formed with the duo-mold imprinting methods of the present invention is limited only by the mechanical strength of the polymer film. If thicker films and tougher polymers are used, wider sealed cavities can be formed. Although such structures have been demonstrated using reversal imprinting over patterned substrates [Bao et al., "Nanoimprinting over topography and multilayer three-dimensional printing," *J. Vac. Sci. Technol. B*, 20:2881-2886, 2002], the duo-mold imprinting eliminates the need to pattern the substrates. Furthermore, the duo-mold imprinting methods of the present invention provide for all-polymeric structures that may be incorporated into all-polymer photonic devices.

EXAMPLE 3

This Example serves to better illustrate how stacked 3-D polymeric micro- or nano-structures can be formed using polymer materials of progressively lower $T_g$.

The duo-mold imprinting of polymers with progressively lower glass transition temperatures or of miscible polymer blends (to tune the transition from glassy behavior to viscoelastic behavior) enable the formation of stacked 3-D structures as illustrated in FIG. 4. A representative three-polymer system suitable for the formation of such stacked 3-D structures is polycarbonate (average MW ~18.2 kg/mol, $T_g$~150° C.), PMMA (average MW ~15 kg/mol, $T_g$~105° C.), and poly(t-butyl-acrylate) (average MW ~100 kg/mol, $T_g$~43° C.). In such a scenario, the first polymer to be imprinted with the duo-mold process would be polycarbonate, followed by PMMA, and finally poly(t-butyl-acrylate).

Alternatively, one could eliminate the use of progressively lower glass transition temperatures for the formation of stacked 3-D structures by using miscible polymer blends with a broader glass transition temperature range. In such cases, imprinting with such a polymer blend could be carried out at a temperature where no change in the shape and form occurs. One such miscible polymer blend that appears to work well for these alternative embodiments is PMMA and poly(vinyl-acetate).

EXAMPLE 4

This Example serves to illustrate a "latch-on" assembly process and mechanism for assembling micro- or nano-meter scale structures according to some embodiments of the present invention.

It is possible to design micro- or nano-meter scale structures that assemble with a latch-on mechanism, similar to that used by Lego® bricks, that would allow the assembly of more complex structures, as shown in FIG. 5. This latch-on scheme of assembly eliminates the need to heat the polymer close to its $T_g$ or use the scheme of stacking polymers with progressively lower glass transition temperatures thus maintaining the shape and form of the structures. It could also enable the assembly of polymers without a $T_g$ such as thermoset plastics and polycrystalline polymers.

EXAMPLE 5

This Example serves to further illustrate potential applications in which the present invention may find use.

Figure 7:
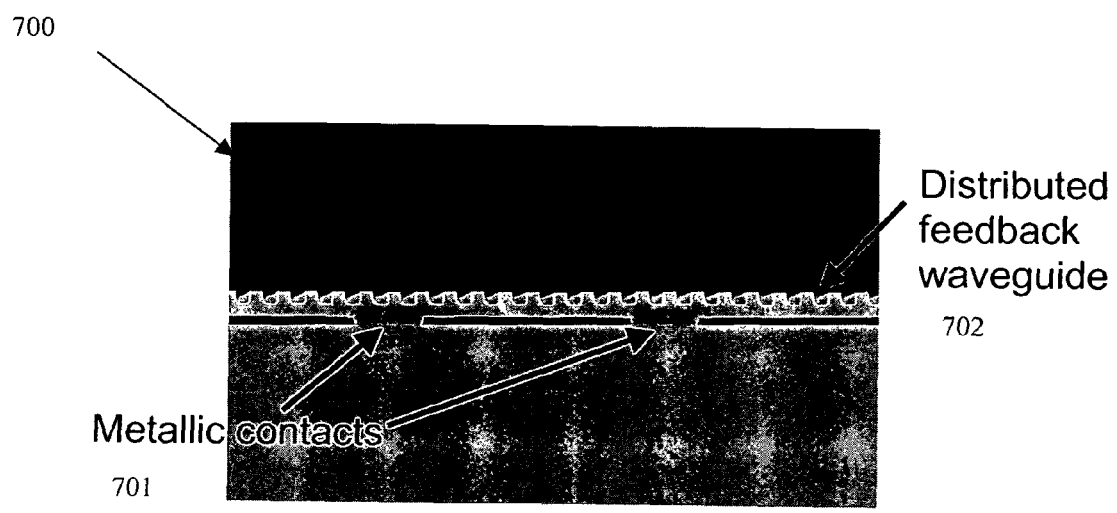
FIG. 7 depicts a scenario wherein the present invention could provide for an electrically-pumped polymer laser with reduced metallic contact.

Potential applications of the methods of the present invention include a scenario wherein the present invention could provide for an electrically-pumped polymer laser with reduced metallic contact, as shown in FIG. 7, wherein device 700 comprises metallic contacts 701 and distributed feedback waveguide 702. Such metal-backed polymer lasers have been developed (Andrew et al., "Photonic band structure and emission characteristics of a metal-backed polymeric distributed feedback laser," *Appl. Phys. Lett.*, 81:954-956, 2002), and recent work in this area suggests that enhanced lasing is obtained when such polymer layers are placed on top of metallic gratings so as to reduce metallic contact. See Stehr et al., "A low threshold polymer laser based on metallic nanoparticle gratings," *Adv. Mater.*, 15:1726-1729, 2003. Such reduced metallic contact is believed to reduce metallic charge absorption.

Figure 8:
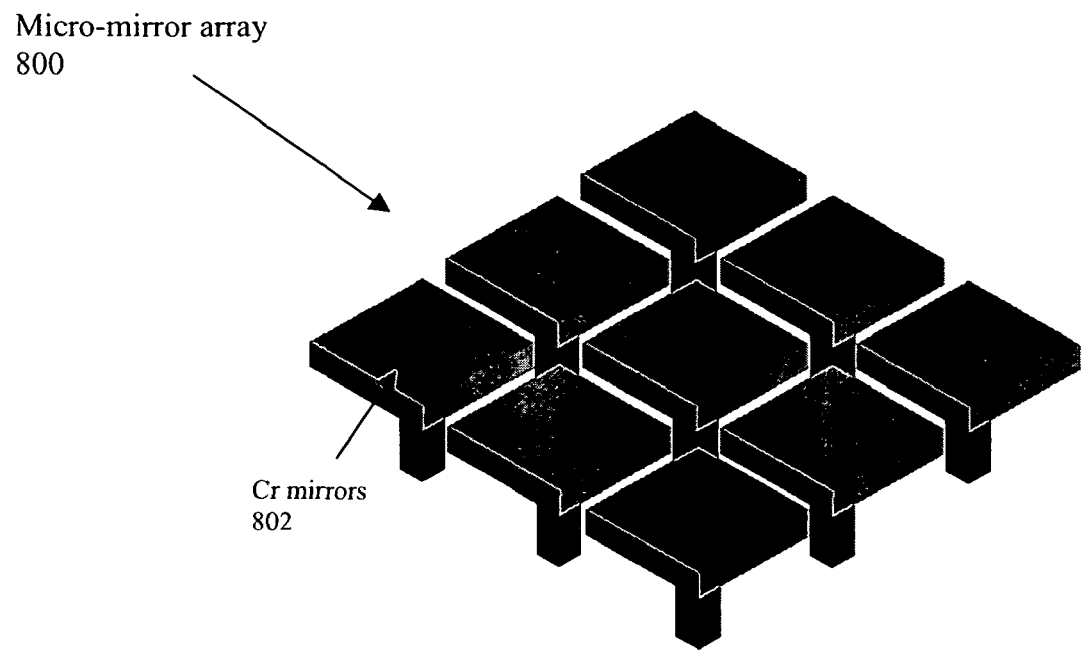
FIG. 8 depicts a scenario wherein the present invention could provide for an array of polymeric micro-mirrors.

FIG. 8 depicts an additional scenario wherein the present invention could provide for an array of polymeric micromirrors 800 comprised of minors (e.g., Cr) 802 on electro-active polymer structures 803, wherein such polymer structures may comprise micro- and/or nanoscale dimensions, and wherein such polymer structures can be fabricated by the imprinting methods described herein. Such micromirrors could be used in digital light processing (DLP™) devices, for example.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method for assembling 3-D polymeric structures, wherein such 3-D polymeric structures are structured such that they comprise features with dimensions that range from the nano-scale to the micro-scale, comprising the steps of:
   a) providing a first 3-D polymeric structure on a substrate;
   b) providing a second 3-D polymeric structure in a surface-treated mold;
   c) pressing the second 3-D polymeric structure into the first 3-D polymeric structure such that the second structure latches onto the first structure; and
   d) separating the surface-treated mold from the second 3-D polymeric structure to provide an assembled structure comprised of the second 3-D polymeric structure on the first 3-D polymeric structure.

2. The method of claim 1 further comprising the steps of:
   a) providing a third 3-D polymeric structure in a second surface-treated mold;
   b) pressing the third 3-D polymeric structure into the second 3-D polymeric structure such that the third structure latches onto the second structure, the second structure being part of the assembled structure;
   d) separating the second surface-treated mold from the third 3-D polymeric structure to provide an augmented assembled structure comprised of the third 3-D polymeric structure on the assembled structure comprising the first and second 3-D polymeric structures.

3. The method of claim 2, wherein the surface-treated molds are silane-treated.

* * * * *